United States Patent
Abbas et al.

(10) Patent No.: US 9,421,136 B2
(45) Date of Patent: Aug. 23, 2016

(54) ABSORBENT ARTICLE COMPRISING A CONTRAPHILIC POLYMER

(75) Inventors: Shabira Abbas, Göteborg (SE); Carolyn Berland, Mölndal (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 1679 days.

(21) Appl. No.: 11/990,121

(22) PCT Filed: Oct. 5, 2005

(86) PCT No.: PCT/EP2005/010736
§ 371 (c)(1),
(2), (4) Date: Feb. 7, 2008

(87) PCT Pub. No.: WO2007/038965
PCT Pub. Date: Apr. 12, 2007

(65) Prior Publication Data
US 2010/0280473 A1     Nov. 4, 2010

(51) Int. Cl.
| A61F 13/15 | (2006.01) |
| A61F 13/53 | (2006.01) |
| A61F 13/514 | (2006.01) |
| A61L 15/26 | (2006.01) |

(52) U.S. Cl.
CPC ........... *A61F 13/53* (2013.01); *A61F 13/51403* (2013.01); *A61L 15/26* (2013.01)

(58) Field of Classification Search
CPC .................. A61F 13/51403; A61F 2013/426
USPC .................................. 604/361, 364, 367, 369
See application file for complete search history.

(56) References Cited

U.S. PATENT DOCUMENTS

| | | | |
|---|---|---|---|
| 3,528,421 A * | 9/1970 | Vaillancourt et al. | 604/372 |
| 3,576,039 A * | 4/1971 | Roberts | 5/484 |
| 3,870,593 A * | 3/1975 | Elton | A61L 15/425 128/889 |
| 4,304,234 A | 12/1981 | Hartmann | |
| 4,327,730 A * | 5/1982 | Sorensen | 604/370 |
| 4,804,378 A | 2/1989 | Shiba et al. | |
| 4,816,320 A * | 3/1989 | St. Cyr | A47K 10/16 15/104.93 |
| 4,923,453 A * | 5/1990 | Bullard, Jr. | 604/356 |
| 5,183,707 A * | 2/1993 | Herron et al. | 428/364 |
| 5,268,229 A * | 12/1993 | Phillips et al. | 428/400 |
| 5,447,788 A * | 9/1995 | Rhim et al. | 442/346 |
| 5,505,718 A * | 4/1996 | Roe et al. | 604/368 |
| 5,508,036 A * | 4/1996 | Bakker et al. | 424/424 |
| 5,558,655 A | 9/1996 | Jezzi et al. | |
| 5,580,348 A * | 12/1996 | Blaney et al. | 604/367 |
| H1657 H * | 6/1997 | Hammons et al. | 604/385.05 |
| 5,658,268 A * | 8/1997 | Johns et al. | 604/361 |
| 5,660,788 A * | 8/1997 | Gray | A61F 13/15731 264/504 |
| 5,869,172 A * | 2/1999 | Caldwell | 428/306.6 |
| 5,955,187 A * | 9/1999 | McCormack et al. | 428/315.5 |
| 5,972,505 A * | 10/1999 | Phillips et al. | 428/397 |
| 6,267,842 B1 * | 7/2001 | Ona | A61K 8/0208 162/112 |
| 6,277,104 B1 * | 8/2001 | Lasko | A61F 13/512 604/368 |
| 6,383,609 B1 | 5/2002 | Annergren et al. | |
| 6,488,670 B1 * | 12/2002 | Schild et al. | 604/385.24 |
| 7,235,145 B2 | 6/2007 | Gfeller et al. | |
| 2001/0014796 A1 * | 8/2001 | Mizutani et al. | 604/367 |
| 2002/0150678 A1 * | 10/2002 | Cramer et al. | 427/212 |
| 2003/0050618 A1 * | 3/2003 | Kondo et al. | 604/383 |
| 2003/0093046 A1 * | 5/2003 | Kim et al. | 604/367 |
| 2003/0153227 A1 * | 8/2003 | Nihlstrand et al. | 442/118 |
| 2003/0153894 A1 * | 8/2003 | Gibbs et al. | 604/386 |
| 2003/0161995 A1 * | 8/2003 | Kauschke et al. | 428/138 |
| 2004/0158214 A1 | 8/2004 | Ponomarenko et al. | |
| 2005/0070866 A1 * | 3/2005 | Isele et al. | 604/367 |
| 2005/0084652 A1 * | 4/2005 | Bonelli | 428/137 |
| 2005/0084682 A1 | 4/2005 | Gfeller et al. | |
| 2005/0084683 A1 | 4/2005 | Wynne | |
| 2005/0282997 A1 * | 12/2005 | Ward et al. | 528/403 |
| 2006/0094320 A1 * | 5/2006 | Chen et al. | 442/340 |
| 2007/0237937 A1 * | 10/2007 | Aizenberg et al. | 428/221 |
| 2010/0042062 A1 * | 2/2010 | Fernkvist et al. | 604/361 |

FOREIGN PATENT DOCUMENTS

| EP | 0 631 768 | 1/1995 |
| EP | 0 640 330 | 3/1995 |
| EP | 0 748 342 B1 | 12/1996 |
| EP | 0 774 242 | 5/1997 |
| EP | 0 878 481 | 11/1998 |
| JP | S62-261363 A | 11/1987 |
| JP | H08-511973 A | 12/1996 |

(Continued)

OTHER PUBLICATIONS

Makal et al., "Water Induced Hydrophobic Surface" Langmuir 2005, vol. 21, pp. 3742-3745.
Sun et al., "Reversible Switching Between Superhydrophilicity and Superhydrophobicity" Angewandte Chemical Int., 2004, vol. 43, pp. 357-360.
International Search Report and the Written Opinion of the International Searching Authority mailed in related International Patent Application No. PCT/EP2005/010736 on Nov. 14, 2006.
Decision on Grant Patent for Invention issued in corresponding Russian Application No. 2008117416 dated Nov. 10, 2009.
Notification of Reason for Rejection issued Oct. 5, 2010, in corresponding Japanese Patent Application No. 2008-533874.

*Primary Examiner* — Paula L. Craig

(74) *Attorney, Agent, or Firm* — Buchanan Ingersoll & Rooney PC

(57) ABSTRACT

An absorbent article such as a diaper, panty diaper, panty liner, a sanitary napkin, an incontinence protection or the like, having in this order a liquid-permeable coversheet, optionally at least one further layer of a web or foam material, optionally an absorbent layer, and a liquid-impermeable coversheet, characterized in that at least one part of this absorbent article has a polymer that is hydrophilic when dry, but shows a reduced hydrophilicity upon wetting; and to the corresponding liquid-permeable or -impermeable coversheet and web or foam material.

20 Claims, No Drawings

(56) References Cited

FOREIGN PATENT DOCUMENTS

| | | |
|---|---|---|
| JP | H08-511974 A | 12/1996 |
| JP | H10-500148 T | 1/1998 |
| JP | H10-330519 A | 12/1998 |
| JP | 2002-532153 A | 10/2002 |
| JP | 2003-175074 A | 6/2003 |
| JP | 2005-513193 T | 5/2005 |
| WO | WO 95/01146 A1 | 1/1995 |
| WO | WO 95/01147 | 1/1995 |
| WO | WO 99/01099 | 1/1999 |
| WO | WO 00/35502 | 6/2000 |
| WO | WO 01/15649 | 3/2001 |
| WO | WO 2004/071342 A2 | 8/2004 |

* cited by examiner

ABSORBENT ARTICLE COMPRISING A CONTRAPHILIC POLYMER

The present disclosure relates to an absorbent article such as a diaper, panty diaper, panty liner, a sanitary napkin, an incontinence device or the like comprising at least one part modified in its hydrophilicity/hydrophobicity response by a new polymer type. This modified part can be a coversheet (topsheet or backsheet) or at least one correspondingly modified underlying web or foam layer ("acquisition/distribution layer").

BACKGROUND

Absorbent articles of the present kind generally comprise a liquid pervious coversheet (topsheet) that is located adjacent the wearer's body, a liquid impervious coversheet (backsheet) that is located distant from the wearer's body and adjacent the wearer's clothing and an absorbent layer interposed between the liquid pervious topsheet and the liquid impervious backsheet. Sometimes however, in specific absorbent articles, the absorbent layer can also be renounced to.

As liquid-permeable coversheets (topsheets), it is customary to use nonwovens and perforated film materials. Both are generally made from inherently hydrophobic, synthetic polymer materials such as polyethylene or polypropylene. To provide these materials with wettability and to enhance liquid permeability, they are typically treated with wetting agents (surfactants).

The treatment with wetting agents renders the inherently hydrophobic material hydrophilic. In some aspects, this treatment is not satisfying. First of all, care must be taken that the wetting agent is firmly bound to the topsheet surface since otherwise already the first insults of body fluid (urine) can wash off the wetting agent. Further, the binding of wetting agents to the topsheet surface also makes the topsheet surface prone to absorb moisture which may cause an unpleasant "wet feel" for the wearer of the absorbent article. Moreover, it would be desirable to provide a topsheet material that also exerts a certain barrier function against rewet from the absorbent core if the same has reached or exceeded its absorption capacity. Hydrophilic topsheet materials, however, are hardly capable of contributing to the fluid management after absorption.

An improved fluid management, superior surface dryness and/or lower rewet can be achieved by inserting fluid management layers, partially also referred to as "acquisition/distribution layers" between the topsheet and the absorbent core, optionally in combination with means for increasing the absorption capacity of the absorbent core, for instance the use of superabsorbent polymers (SAP). This is taught for instance by U.S. Pat. No. 5,558,655, EP 0 640 330 A1, EP 0 631 768 A1, WO 95/01147 or WO 00/35502. However, even the use of high performance liquid/acquisition distribution layers is not capable of overcoming the afore-mentioned disadvantages. To achieve a superior surface dryness it is also known from EP 1 003 454 A1 in the name of the present applicant to use liquid-permeable coversheets comprising one hydrophilic and one hydrophobic material layer. The first material layer is plasma- or corona-treated and has a hydrophilic surface and is situated far away from the wearer. The second material layer is made from an inherently hydrophobic material being in contact with the skin of the wearer, which means that this surface remains dry even after wetting. In this embodiment of EP 1 003 454 A1, the first material layer, that is the inner fiber structure functions as drainage material which has the ability to drain liquid from the upper (second) layer nearest the user.

In view of the above, it is one technical object of the present disclosure to provide an absorbent article with improved surface dryness.

It is one further technical object of the present disclosure to provide an absorbent article showing optimal hydrophilic/hydrophobic properties for achieving a good fluid management upon wetting.

It is one further technical object of the present disclosure to provide an absorbent article showing a barrier function against rewet from the absorbent body.

It is one further object of the present disclosure to achieve the above aims with as few material layers as possible.

BRIEF SUMMARY

The present disclosure relates to an absorbent article such as a diaper, panty diaper, panty liner, a sanitary napkin, an incontinence device or the like, comprising in this order
  a liquid-permeable coversheet,
  optionally at least one further layer of a web or foam material,
  optionally an absorbent layer, and
  a liquid-impermeable coversheet,
characterized in that at least one part of the absorbent article comprises a polymer (in the following also referred to as "contraphilic" polymer) that is hydrophilic when dry, but shows a reduced hydrophilicity, preferably hydrophobicity upon wetting. "One part of the absorbent article comprises a polymer" means that this part has been made from a contraphilic polymer or that this part was treated (for instance coated) with a contraphilic polymer, which is then preferably present as polymer layer on this part of an absorbent article.

The part comprising the contraphilic polymer is preferably the liquid-permeable cover-sheet (topsheet), optionally the at least one further layer of a web or foam material or the liquid-impermeable coversheet (backsheet).

The disclosure also extends to a corresponding topsheet, backsheet, web or foam material comprising a polymer that is hydrophilic when dry, but shows a reduced hydrophilicity upon wetting.

The use of a contraphilic polymer in the manufacture of diaper parts, such as in topsheets or the underlying at least one further layer leads to remarkable benefits in the performance of absorbent articles. The wetting by incoming body liquids is enhanced by the hydrophilic nature of contraphilic polymers in a dry state. Simultaneously, incoming body liquid is more easily drained due to the change to less hydrophilic (more hydrophobic) properties upon wetting.

A coating of a contraphilic polymer on at least one side of a backsheet (preferably that side facing the wearer) allows the use of very open, breathable materials. This is because the material is hydrophilic when dry and thus will readily allow the passage of water vapour. Upon exposure to liquid water, the contraphilic polymer will become hydrophobic and prevent the passage of water drops.

Moreover, the reduced hydrophilicity (increased hydrophobicity) of the topsheet or the further layer(s) upon wetting facilitates drying of the contraphilic surface thereby avoiding the unpleasant wet feel of some hydrophilic materials. In addition, the change to less hydrophilic (more hydrophobic) properties will create a barrier function against liquid leaking out from the absorbent layer (rewet) thereby increasing the dryness of the topsheet surface being in contact with the wearer's skin.

DETAILED DESCRIPTION OF PREFERRED EMBODIMENTS

As "hydrophobic" the art typically understands a material or a portion of a molecule made of a specific material that upon wetting of a smooth flat surface solely consisting of this material with water leads to sessile drop contact angles greater than 90°. Conversely, a smooth flat surface (where no effects due to surface roughness occur) that leads to contact angles of a sessile water drop of less than 90°, or where the water drop spreads spontaneously across the surface, is typically considered as "hydrophilic". This is also the preferred understanding to be applied in the present disclosure. The contact angle can be determined in line with TAPPI method T558PM-95 (1995) under consideration of the following:

1. The materials to be tested should be acclimatized at 23° C., 50% relative humidity over a suitable period of time (at least 4 h) prior to measurement. The measurement must be performed in a climate-controlled room (23° C., 50% relative humidity).
2. The materials to be tested should be present as a single layer of material which can be applied to a standard sample holder using double sided adhesive tapes, as for instance recommended by the manufacture.
3. Suitable parameters for the measurement are:
   a) liquid, reagent quality water
   b) a drop volume of 5 µl
   c) number of drops to be measured for averaging the results: 25
   d) in the hypothetical case where neither T558PM-95 nor the present comments address specific measurement conditions, default values as recommended by the manufacturer of the testing equipment can be used. Names of suppliers of suitable testing equipment may be found in the bound set of TAPPI test methods or may be availably from the TAPPI information resources centre. Preferred devices are manufactured by Fibro System AB, Stockholm and are marketed under the FibroDat® Trademark, such as FibroDat 1100 contact angle tester.
4. For those materials (e.g. hydrophilic, absorbent materials) where the contact angle varies with time, the measurement is conducted 0.05 sec after deposition of the drop.
5. For extremely hydrophobic surfaces the contact angle measurement may fail due to the drop beading up and rolling off the test surface. These surfaces are considered superhydrophobic.

As "absorbent article" we understand articles capable of absorbing body fluids such as urine, watery feces, female secretion or menstrual fluids. These absorbent articles include, but are not limited to diapers, panty diapers, panty liners, sanitary napkins or incontinence devices (as for instance used for adults).

Such absorbent articles have a liquid-pervious coversheet (topsheet) which during use is facing the wearer's body. They further comprise a liquid-impervious coversheet (backsheet), for instance a plastic film, a plastic-coated nonwoven or a hydrophobic nonwoven and preferably an absorbent layer enclosed between the liquid-pervious topsheet and the liquid-impervious backsheet. In some absorbent products without absorbent layer, such as specific panty liners marketed by the present applicant under various trademarks in connection with the product name "Freshness everyday", the absorbent capacity of topsheet and backsheet is sufficient to absorb small amounts of female secretion.

Optionally, at least one further layer of a web or foam material is arranged between the absorbent layer and the topsheet. The at least one further layer may for instance
   be joined with the topsheet to form a multi-layer topsheet,
   aid in removing body liquids penetrating through the topsheet and/or distributing the incoming body liquids over the entire surface of the absorbent layer, as in so-called "acquisition/distribution layers", or
   belong to the core wrap of the absorbent layer.

Specifically, it may be at least one layer of a web or foam material that is effective in quickly conducting incoming liquid further away from the topsheet and spreading the liquid in perpendicular direction to the topsheet surface to make optimum use of the available surface of the absorbent body.

According to one embodiment of the disclosure, the liquid-permeable coversheet (topsheet) comprises the polymer that is hydrophilic when dry, but shows a reduced hydrophilicity, preferably hydrophobicity upon wetting ("contraphilic" polymer).

A suitable topsheet may be manufactured from a wide range of materials such as woven and nonwoven materials (e.g. a nonwoven web of fibers), polymeric materials such as apertured plastic films, e.g. apertured formed thermoplastic films and hydroformed thermoplastic films; porous foams; reticulated foams; reticulated thermoplastic films; and thermoplastic scrims. Suitable woven and nonwoven materials can be comprised of natural fibers or from a combination of natural and synthetic fibers. Examples of suitable synthetic fibers which may comprise all or part of the topsheet include but are not limited to polyamide (e.g. nylon), acrylic (e.g. polyacrylonitrile), aromatic polyamide (e.g. aramide), polyolefin (e.g. polyethylene and polypropylene), polyester, butadiene-styrene block copolymers, natural rubber, latex, spandex (polyurethane) and combinations thereof. Synthetic fibers that contain more than one type of repeat unit can result from combining repeat units at the molecular level within each macromolecular strand (copolymer), between macromolecular strands (homopolymer blends), or combinations thereof (co-polymer blends); or they can result from combining repeat units at a higher scale level with distinct nanoscopic, microscopic, or macroscopic phases (e.g., multicomponent fibers). Each component of a multicomponent fiber can comprise a homopolymer, a copolymer, or blends thereof. Bicomponent fibers are common versions of multicomponent fibers. The two or more types of repeat units in a copolymer can be arranged randomly or in alternating blocks of each type. Blocks of different types of repeat units can jointed to one another at their respective ends (block co-polymers) or between the respective end of at least one block (graft co-polymers).

Nonwoven materials can be formed by direct extrusion processes during which the fibers and the nonwoven materials are formed at about the same point in time, or by preformed fibers which can be laid into nonwoven materials at a distinctly subsequent point in time. Exemplary direct extrusion processes include but are not limited to: spunbonding, melt-blowing, solvent spinning, electrospinning and combinations thereof typically forming layers. Exemplary "laying" processes including wet laying and dry laying. Exemplary dry laying processes include but are not limited to air laying, carding and combinations thereof typically forming layers. Combinations of the above processes yield nonwovens commonly called hybrids or composites.

The fibers in a nonwoven material are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. A more detailed description of suitable topsheet materials which can be applied to the present disclosure and is incorporated by reference is found in US 2004/0158214 A1, specifically in the passage from paragraphs [0043] to [0051].

In accordance with the disclosure, it is preferred to make use of apertured plastic films (e.g. thermoplastic films) or nonwoven materials based on synthetic fibers, e.g. those made from polyethylene or polypropylene homo- or copolymers and polymer compositions based thereon.

According to a second embodiment of the disclosure, the at least one further layer provided between the topsheet and the absorbent layer comprises the contraphilic polymer.

If present, the at least one further layer existing between the absorbent layer and the topsheet may be selected from hydrophobic and hydrophilic web and foam materials. As "web material" we understand coherent flat fiber-based structures of paper tissue, woven or nonwoven type. The nonwoven material may have the same features as described above for topsheets.

Specifically, the at least one further layer may contribute to fluid management, for instance in the form of at least one acquisition/distribution layer. Such structures are taught for instance by U.S. Pat. No. 5,558,655, EP 0 640 330 A1, EP 0 631 768 A1, WO 95/01147 or WO 00/35502.

"Foam materials" are also well known in the art and for instance describe in EP 0 878 481 A1 or EP 1 217 978 A1 in the name of the present applicant.

The optional absorbent layer may comprise any absorbent material that is generally compressible, conformable, non-irritating to the wearer's skin and capable of absorbing and retaining liquids such as urine and other body exudates. The absorbent layer may be partially or totally surrounded by a core wrap. In some specific products it may also be totally omitted.

The absorbent layer may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (such as superabsorbent fibers), absorbent gelling materials, or any other known absorbent materials or combinations of materials. Examples of some combinations of suitable absorbent materials are fluff with absorbent gelling materials and/or superabsorbent polymers, and absorbent gelling materials and superabsorbent fibers etc.

The backsheet prevents the exudates absorbed by the absorbent layer and containing with the article from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films.

Any of the above absorbent article parts, such as the topsheet and/or the at least one further layer and/or the backsheet comprises a polymer that is hydrophilic when dry, but shows a reduced hydrophilicity, preferably hydrophobicity upon wetting. In this connection, "comprising" means that the corresponding absorbent article part can be made from this polymer or carry a coating thereof. This coating can cover the entire surface of the article part or only a portion thereof.

Generally, it is preferred to coat that surface of the topsheet or the "at least one further layer" that faces the skin of the wearer. Techniques known in the art can be used for applying the coating on the article part. These include the application of an organic solution of the polymer by means of spraying, printing or roller coating, or by dipping the topsheet/layer into the organic solution followed by evaporation of the solvent. Suitable solvents for preparing the organic solution are compatible with the substrate (topsheet/layer/backsheet) to be coated and can be selected from polar protic and aprotic solvents. These preferably have a boiling point of less than 120° C. at normal pressure to allow easy removal from the solution. Suitable solvents can be selected from monoalcohols, polyhydric alcohols such as ethyleneglycol or propyleneglycol, cellosolve, ethers such as THF, ketones such as acetone or hexafluoroacetone, organic amides such as DMF or dimethylacetamide, and organic sulfoxides such as DMSO, THF being preferred.

The part of the absorbent article to be coated with the contraphilic polymer may also be subjected to a plasma or corona treatment as known in the art. Such treatment may improve the adhesion of the contraphilic polymer in its original hydrophilic state to hydrophobic materials as used for topsheets, backsheets or the at least one further layer.

Polymers showing the required hydrophilicity/hydrophobicity switching upon wetting are known from the art, specifically from US 2005/0084683 A1 and U. Makal and K. J. Wynne "Water induced hydrophobic surface", Langmuir 2005, 21, 3742-3745. Because of their unusual response to wetting—most materials become more hydrophilic upon wetting—they are named "contraphilic" polymers. Preferably, they show a fully reversible change from hydrophilic to less hydrophilic properties, in particular hydrophobic properties. That is after drying the surface displays again the original contact angle characteristics of a hydrophilic coating. Preferably, the contact angle of a sessile water drop vis-á-vis a smooth surface of the material constituting the topsheet/layer/backsheet changes by at least 5°, more preferably by at least 10°, even more preferably by at least 15°, in particular by at least 20° upon wetting. The sessile drop contact angle is measured as stated above.

According to one embodiment of the present disclosure, the sessile drop contact angle is from 60 to less than 90°, in particular from 75 to 85° prior to wetting and more than 90 and up to 120°, in particular 100 to 110° after wetting.

According to one further embodiment of the present disclosure fine particles are used to increase the hydrophobicity of a coating of the contraphilic polymer due to an increased surface roughness. Values corresponding to contact angles of more than 120°, in particular more than 135°, or even more than 150° (superhydrophobicity) can be reached thereby. Simultaneously, it is possible to increase the hydrophilicty to values below 60°, in particular below 45° or even below 30° (superhydrophilicity). From T. Sun et al. "Reversible switching between superhydrophilicity and superhydrophobicity", Angewandte Chemie Int. 2004, 43, 357-360, it is known that increasing surface roughness leads to the desired switching between superhydrophilicity and superhydrophobicity.

One option to achieve the desired surface roughness would involve incorporating the fine particles into the coating solution of the contraphilic polymer.

A second and preferred option requires applying first a dispersion of any suitable polymer and the fine particles to form an underlayer having surface roughness followed by the evaporation of the solvent. Then a solution or dispersion of the contraphilic polymer is applied in a thin layer, which may even be monomolecular, whereafter the solvent (e.g. the same as indicated before) is again evaporated.

Independently of the application technique, the fine particles are incorporated into the coating solution in amounts based on the (contraphilic) polymer that increase the surface roughness of the resulting coating. Suitable amounts can be easily determined by a skilled person.

The particles to be incorporated are preferably spherical and may for instance have diameters in the range from 100 nm to 1000 µm (e.g. 500 nm to 500 µm, 800 nm to 100 µm, 1 µm to 50 µm or 2 µm to 10 µm). From the article of T. Sun it would appear that spacings between groves of about 6 µm are particularly suitable to achieve a switching between superhydrophilicity and superhydrophobicity. The coating solution may contain amounts of particles solution that lead to a complete surface coverage, and thereby to contact between individual particles. It can be easily verified by contact angle measurements whether or not the switching between superhydrophilicity and superhydrophobicity occurs for a given type and amount of particles.

The particles to be incorporated into the coating can be selected from polymeric particles which are preferably inert towards the coating solvent and/or inorganic particles such as metal or oxide particles which can be optionally surface modified (e.g. to generate hydrophobic coatings) to increase their compatibility, if necessary. Alumina, iron oxide or zirconia nanoparticles are for instance available from Nanotechnologies, Inc., USA. Hydrophilic and hydrophobic silica nanoparticles are available under the Aerosil® trademark. Uncounted examples for commercially available polymeric nanoparticles exist, one being acrylic nanoparticles (e.g. with a size of 50 to 150 nm) as manufactured by ElizaNor Polymer LLC, USA. Moreover, non-spherical nanoparticles such as clay minerals may also be used.

The use of a contraphilic polymer in the manufacture of topsheets or the underlying at least one further layer leads to remarkable benefits in the performance of absorbent articles. The wetting by incoming body liquids is enhanced by the hydrophilic nature of contraphilic polymers in a dry state. Simultaneously, incoming body liquid is more easily drained due to the change to less hydrophilic properties upon wetting. This behaviour is in accordance with the fact that high receding contact angles, i.e. a hydrophobic character enhance the removal of droplets of a liquid front from a surface. Moreover, the increased hydrophobicity of the topsheet or the further layer(s) upon wetting facilitates drying of the contraphilic surface thereby avoiding the unpleasant wet feel of some hydrophilic materials. In addition, the change to less hydrophilic properties will create a barrier function against liquid leaking out from the absorbent core (rewet) thereby increasing dryness of the topsheet surface being in contact with the wearer's skin.

A coating of a contraphilic polymer on at least one side of a backsheet (preferably that side facing the wearer) allows the use of very open, breathable materials. This is because the material is hydrophilic when dry and thus will readily allow the passage of water vapour. Upon exposure to liquid water, the contraphilic polymer will become hydrophobic and prevent the passage of water drops.

The coating solution does not need to contain the contraphilic polymer as sole polymer constituent. Since, in line with US 2005/0084683 A1, contraphilic polymers show a tendency to be enriched in the surface domain, the contraphilic polymer may also be used as a minor polymer constituent by weight, for instance in an amount of less than 10, or less than 5 wt. %, for instance 0.1 to 3 wt. %, based on all polymer materials in the coating solution. The contraphilic behaviour is preferably brought about by certain types of side chains as explained below in further detail. Therefore, contraphilic polymers are not specifically limited regarding their backbone structure and for instance polyurethanes, polyesters, polyethers, polyamides, polyimides, in particular polyurethanes can be used. If the contraphilic polymer is used in admixture with a non-contraphilic polymer, both show preferably the same backbone structure.

The contraphilic polymer to be used preferably comprises soft and hard segments. The soft segment preferably has a glass transition temperature of less than 0° C., as measured by DSC under the conditions given in US 2005/084683 A1. Preferred glass transition temperatures of the soft segment range from −5 to −60° C. The glass transition temperature Tg of the hard segment (measured under the same conditions) is preferably more than 20° C., in particular 30 to 95° C.

The ratio of hard/soft segments is preferably 25 to 60 wt. %/75 to 40 wt. %, more preferably 35 to 45 wt. %/65 to 55 wt. %.

In the case of polyurethanes, the hard block is preferably prepared from diisocyanates and diols and/or diamines, for instance isophorone diisocyanate (IPDI) and 1,4-butandiol (BD).

The soft block preferably comprises
a) at least one hydrophobic side chain having at least one hydrogen atom and
b) at least one side chain having a functional group capable of forming a hydrogen bond with the at least one hydrogen atom of the hydrophobic side chain.

A random, in particular an at least partially alternating arrangement of side chains (a) and (b) seems to be preferred.

The hydrophobic side chain (a) is preferably selected from optionally substituted hydrocarbon groups (including isomeric hydrocarbon groups) having preferably 1 to 22 carbon atoms, for instance 3 to 18 carbon atoms, or 5 to 14 carbon atoms, siloxane groups such as trimethylsilyl having preferably not more than 10 silicon atoms.

The substituted hydrocarbon group preferably comprises a hydrogen-bond donor. Hydrogen-bond donors are moieties that contain at least one hydrogen atom that can participate in hydrogen-bond formation and a more electronegative atom bound to the hydrogen atom. Examples of these moieties include, but are not limited to, O—H, N—H, P—H, and S—H. These moieties can be present in any functional group. The number (preferably only one), position and type of these moieties are preferably selected under consideration of the capacity to form hydrogen bonds and the hydrophobic character of the side chain (a) to be achieved. The moiety C—H can also be a hydrogen-bond donor if the carbon atom is bound to another atom through a triple bond, if the carbon atom is bound through a double bond to O, or if the carbon atom is bound to at least two atoms selected from O, F, Cl, and Br.

Example of suitable substituted hydrocarbon chains are semifluorinated hydrocarbon groups such as —$(CH_2)_n$ $(CF_2)_m$F or —$(CH_2)_n(CF_2)_m$H wherein each $CH_2$ unit may also be replaced by (CHF) and n is typically 1 to 10 and m is typically 1 to 12, the preferred total carbon number being 1 to 10, in particular 2 to 7.

The functional group of side chain (b) is capable of forming a hydrogen bond with the at least one hydrophobic side chain (a). It represents preferably a hydrogen-bond acceptor, that is a moiety that contains an atom more electronegative than hydrogen which can also contain a lone pair of electrons. Examples of such atoms include, but are not limited to N, O, F, Cl, Br, I, S, and P. Examples of this functional group include ketone, aldehyde, ester, amide or imide. These functional groups may also be present in cyclic form, for instance in ring systems having 4 to 7 ring atoms as in hydantoins, e.g. 5,5-dimethylhydantoin.

Without wishing to be bound by theory, it is believed that contraphilic behaviour can be most easily achieved with polymers having side chains (a) and (b) based on a mechanism described in the Makal reference. In the dry state, inter- or intramolecular hydrogen bonding between side chain (a) and (b) disrupts the usual surface concentration of hydrophobic side chain (a), in particular semi-fluorinated side chain (a). Upon surface hydration, the functional group, preferably an amide group prefers to hydrogen bond with water rather than the hydrogen atom of hydrophobic side chain (a). With the introduction of water, the hydrophobic side chain (a) is "released" and the surface becomes hydrophobic. If the surface is dehydrated, it returns again to its initial hydrophilic state.

The main chain of the soft segment is preferably of polyether type which can be linked by corresponding moieties (e.g. urethane moieties) to the hard segment. A preferred polyether soft segment is of polyalkyleneoxy type, wherein the single alkyleneoxy unit has preferably 2 to 20, more preferably 3 to 7, in particular 4 to 6 carbon atoms, as in 2,2-dimethyl-substituted 1,3-propylene oxide.

Such polyether soft segments are for instance obtainable by polymerization of the corresponding epoxy compounds or ring-opening polymerisation of cyclic precursors, such as oxetanes for 1,3-propyleneoxy units.

To allow functionalization, i.e. attachment of side chains (a) and (b), at least a part of the soft segment precursors (monomers) preferably carries at least one leaving group (X), such a halogen (Cl, Br) as in 3-bromomethyl-3-methyloxetane.

To achieve the preferred random arrangement of side chains (a) and (b), the soft block segment is prepared from mixtures of alkyleneoxy precursors (monomers) such as oxetanes wherein one precursor still carries the leaving group X while the other precursor is obtainable by substituting X for side chain (a) or (b). The resulting intermediates carrying side chain (a) are then treated with a side chain precursor for (b) and vice versa as described in US 2005/0084683 A1 and the Makal reference. The side chain precursors preferably carry aprotic and nucleophilic functional group such as O—H or N—H capable of substituting the leaving group X. Alternatively, it is also possible to polymerise the alkyleneoxy precursor followed by reaction with a mixture of side chain precursors (a) and (b).

One embodiment of a contraphilic polymer has the generic formula (3) shown in the following reaction scheme and is obtainable by reacting soft segment (1) with a hard segment obtainable by the reaction of isophorone diisocyanate (IPDI) and 1,4-butane diol (BD). After the preparation of intermediate (2), substitution of the reactive Br-group in —CH$_2$Br with 5,5-dimethylhydantoin (Hy) gives polyurethane (3). Due to incomplete reaction, minor amounts of the unconverted Br-containing side chain may still be present. Concretely, the composition of polyurethane (3) can be described as IPDI-BD-(40)/P (5FOx/HyOx/BrOx=2.0:0.7:0.3) (5,000) with IPDI-BD hard block followed by weight % in parenthesis; soft block segment ratios p=2, y=0.7 and remaining —CH$_2$Br=0.3, HyOx, the hydantoin-substituted repeat; and Mn following in parenthesis.

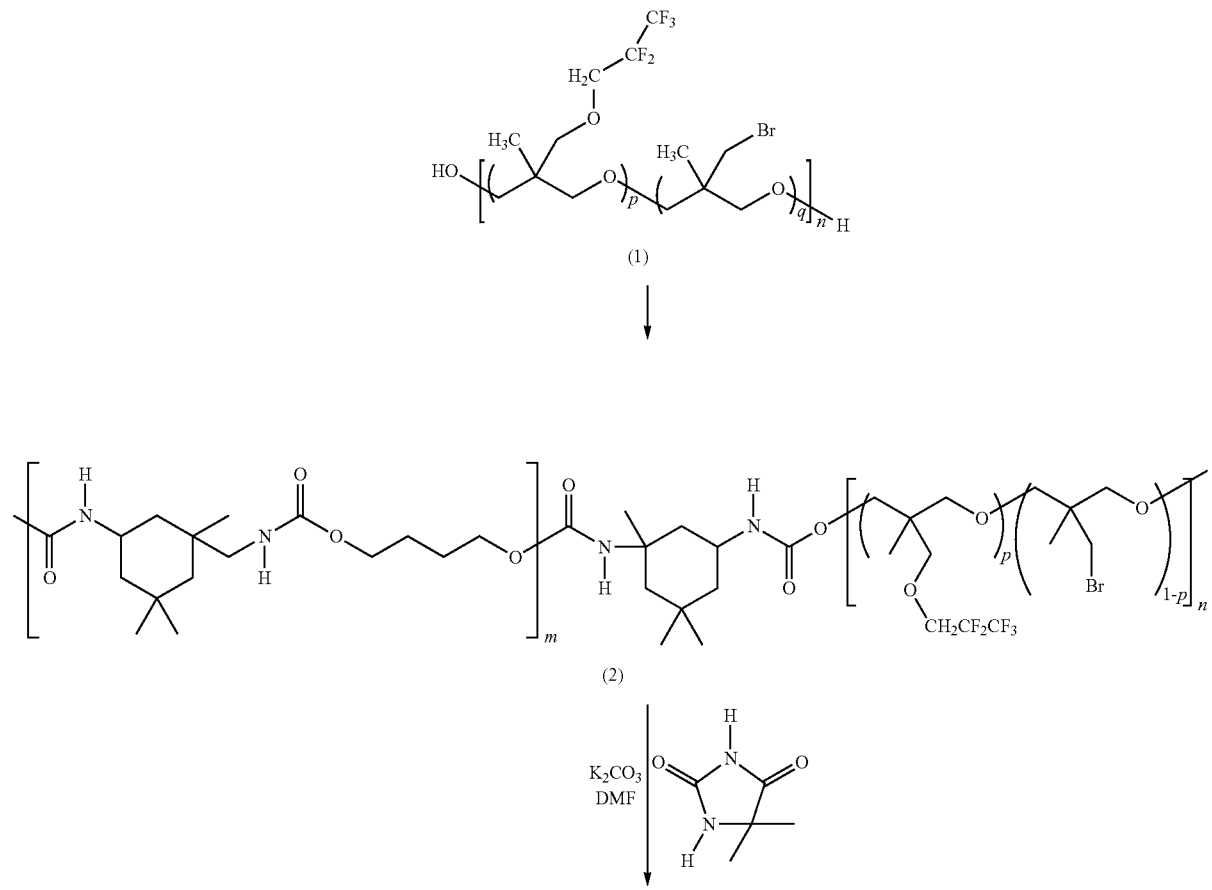

-continued

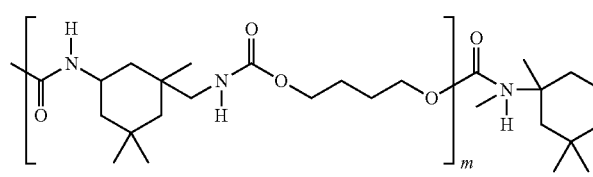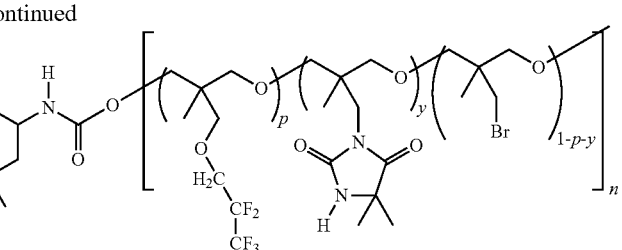

(3)

Generally, the molecular weight of the contraphilic polymer is preferably at least 20,000, preferably 30,000 to 100,000 and the molecular weight of the soft segment preferably ranges from 1,000 to 10,000, preferably 2,000 to 7,000, both as measured in line with US 2005/0084682 A1.

The present disclosure also relates to a liquid-permeable coversheet (topsheet), a web or foam material, or a backsheet comprising the above contraphilic polymer.

The invention claimed is:

1. An absorbent article comprising in this order
a liquid-permeable coversheet, and
a liquid-impermeable coversheet,
wherein at least one part of the absorbent article comprises a coating comprising a contraphilic polymer that is hydrophilic when dry, but shows a reduced hydrophilicity upon wetting, and
wherein the coating comprises fine particles and the surface roughness of the coating is increased by the fine particles.

2. The absorbent article according to claim 1 wherein the change from hydrophilic to less hydrophilic is reversible.

3. The absorbent article according to claim 1 wherein the part of the absorbent article comprising the contraphilic polymer becomes hydrophobic upon wetting.

4. The absorbent article according to claim 1 wherein the contact angle of a sessile water drop vis-à-vis the contraphilic polymer changes by at least 10° upon wetting.

5. The absorbent article according to claim 1 wherein the contact angle of a sessile water drop vis-à-vis the contraphilic polymer changes from 60-85° prior to wetting to 95-120° after wetting.

6. The absorbent article according to claim 1 wherein the contraphilic polymer is a block copolymer comprising soft and hard blocks.

7. The absorbent article according to claim 6, wherein the soft block comprises a main chain, at least one hydrophobic side chain (a) having at least one hydrogen atom and at least one side chain (b) having a functional group capable of forming a hydrogen bond with the at least one hydrogen atom of the hydrophobic side chain (a).

8. The absorbent article according to claim 7 wherein the functional group is selected from ketone, aldehyde, ester, amide and imide groups.

9. The absorbent article according to claim 7 wherein the main chain is of polyether type.

10. The absorbent article according to claim 6 wherein the hard segment is of polyurethane type.

11. The absorbent article according to claim 1 comprising in this order
the liquid-permeable coversheet,
at least one further layer of a web or foam material, and
the liquid-impermeable coversheet.

12. The absorbent article according to claim 11, wherein the part of the absorbent article comprising the contraphilic polymer is selected from the liquid-permeable coversheet, the at least one further layer of a web or foam material or the liquid-impermeable coversheet.

13. The absorbent article according to claim 1 comprising in this order
the liquid-permeable coversheet,
an absorbent layer, and
the liquid-impermeable coversheet.

14. The absorbent article according to claim 1 comprising in this order
the liquid-permeable coversheet,
at least one further layer of a web or foam material,
an absorbent layer, and
the liquid-impermeable coversheet.

15. A liquid-permeable coversheet for an absorbent article wherein the liquid-permeable cover-sheet comprises a coating comprising a contraphilic polymer that is hydrophilic when dry, but shows a reduced hydrophilicity upon wetting, and wherein the coating comprises fine particles and the surface roughness of the coating is increased by the fine particles.

16. A web or foam material for a diaper, a panty diaper, a panty liner, a sanitary napkin, or an incontinence device, wherein the web or foam material comprises a coating comprising a contraphilic polymer that is hydrophilic when dry, but shows a reduced hydrophilicity upon wetting, and wherein the coating comprises fine particles and the surface roughness of the coating is increased by the fine particles.

17. The web or foam material for a diaper, a panty diaper, a panty liner, a sanitary napkin, or an incontinence device according to claim 16, wherein the fine particles are spherical and have a diameter in a range from 2 μm to 10 μm.

18. The web or foam material for a diaper, a panty diaper, a panty liner, a sanitary napkin, or an incontinence device according to claim 16, wherein the fine particles are selected from the group consisting of alumina, iron oxide or zirconia nanoparticles, hydrophilic and hydrophobic silica nanoparticles, acrylic nanoparticles, and non-spherical nanoparticles of clay minerals.

19. The web or foam material for a diaper, a panty diaper, a panty liner, a sanitary napkin, or an incontinence device according to claim 16, wherein the fine particles are selected from the group consisting of alumina, iron oxide or zirconia nanoparticles, and hydrophilic and hydrophobic silica nanoparticles.

20. A liquid-impermeable coversheet for an absorbent article wherein the liquid-impermeable cover-sheet comprises a coating comprising a contraphilic polymer that is hydrophilic when dry, but shows a reduced hydrophilicity upon wetting, and wherein said coating comprises fine particles and the surface roughness of said coating is increased by the fine particles.

\* \* \* \* \*